(12) United States Patent
Troxler

(10) Patent No.: US 12,416,585 B2
(45) Date of Patent: Sep. 16, 2025

(54) DEVICES AND METHODS FOR COMMUNICATING MEASUREMENT RESULTS FROM A MEASUREMENT GAUGE

(71) Applicant: Troxler Electronic Laboratories, Inc., Research Triangle Park, NC (US)

(72) Inventor: Robert Ernest Troxler, Research Triangle Park, NC (US)

(73) Assignee: Troxler Electronic Laboratories INC, RTP, NC (US)

( * ) Notice: Subject to any disclaimer, the term of this patent is extended or adjusted under 35 U.S.C. 154(b) by 97 days.

(21) Appl. No.: 18/171,538

(22) Filed: Feb. 20, 2023

(65) Prior Publication Data

US 2023/0384242 A1     Nov. 30, 2023

Related U.S. Application Data

(63) Continuation of application No. 14/484,246, filed on Sep. 11, 2014, now abandoned.

(60) Provisional application No. 61/876,720, filed on Sep. 11, 2013.

(51) Int. Cl.
*G01N 23/00*     (2006.01)
*G01N 33/42*     (2006.01)

(52) U.S. Cl.
CPC ........... *G01N 23/005* (2013.01); *G01N 33/42* (2013.01)

(58) Field of Classification Search
CPC ............................. G01N 23/005; G01N 33/42
See application file for complete search history.

(56) References Cited

U.S. PATENT DOCUMENTS 5,318,459 A     6/1994  Shields
7,376,530 B2    5/2008  Bienvenu et al.

OTHER PUBLICATIONS

USPTO, Non-Final Office Action for corresponding U.S. Appl. No. 14/484,246, mailed Jun. 2, 2016, 26 pages.
USPTO, Final Office Action for corresponding U.S. Appl. No. 14/484,246, mailed Nov. 2, 2016, 28 pages.
National Semiconductor Corporation's LMX9838 Data Sheet, Sep. 2007, 30 pages.
Figs. 3-1 and 3-2 on pp. 3-3 and 3-4 of Troxler Electronic Laboratories, Inc.'s Manual of Operation and Instruction for Model 3451 Enhanced RoadReader™ Plus (Edition 3.Jul. 1, 2009), 2 pages.
USPTO, Non-Final Office Action for corresponding U.S. Appl. No. 14/484,246, mailed Apr. 5, 2017, 33 pages.
USPTO, Final Office Action for corresponding U.S. Appl. No. 14/484,246, mailed Nov. 15, 2017, 33 pages.
USPTO, Non-Final Office Action for corresponding U.S. Appl. No. 14/484,246, mailed Jun. 25, 2018, 38 pages.

(Continued)

*Primary Examiner* — Mark R Gaworecki
(74) *Attorney, Agent, or Firm* — NK Patent Law PLLC

(57) ABSTRACT

A system and related methods and apparatuses are disclosed herein. The system includes a material measurement gauge including a gauge communications module, an adapter configured for communicating with the gauge communications module, the adapter including memory and an adapter communications module, a handheld device operably communicating with the adapter and configured for communicating information, a network in communication with at least one of the adapter and the handheld, and a computing device configured for storing information received from the handheld device and/or the network.

37 Claims, 16 Drawing Sheets

(56) References Cited

OTHER PUBLICATIONS

USPTO, Final Office Action for corresponding U.S. Appl. No. 14/484,246, mailed Dec. 31, 2018, 43 pages.
Motorola, Inc. MC145406/D datasheet, 12 pages (Year: 1995).
Texas Instruments Incorporated, Interface circuits for TIA/EIA-232-F design notes SLLA037 A, 22 pages (Year: 2002).
USPTO, Non-Final Office Action for corresponding U.S. Appl. No. 14/484,246, mailed Jul. 25, 2019, 46 pages.
USPTO, Final Office Action for corresponding U.S. Appl. No. 14/484,246, mailed Dec. 26, 2019, 40 pages.
USPTO, Non-Final Office Action for corresponding U.S. Appl. No. 14/484,246, mailed Jun. 8, 2020, 35 pages.

DEVICES AND METHODS FOR COMMUNICATING MEASUREMENT RESULTS FROM A MEASUREMENT GAUGE

CROSS-REFERENCE TO RELATED APPLICATIONS

This application is a continuation of U.S. Non-Provisional patent application Ser. No. 14/484,246, filed on Sep. 11, 2014, which claims priority to U.S. Provisional Patent Application No. 61/876,720, filed on Sep. 11, 2013, the entire contents of which are all incorporated by reference herein.

TECHNICAL FIELD

This disclosure is directed towards devices and methods for controlling and communicating measurement results from a measurement gauge. In one or more embodiments, the devices are capable of communicating with measurement gauges and communicating acquired information to an external site.

BACKGROUND

Legacy equipment in the field of road construction measurements relies on archaic methods of data transfer, requiring a PC, laptop, serial connector and a terminal program. Other methods include even a writing utensil and a writing pad for recording project information such as operator, date, time, location, density, moisture, modulus to name a few.

In many instances, the measurement gauges being used to conduct one or more measurements have a lengthy service life. As a result, upgrading the gauges to modern standards with modern communications hardware may be desirable, but impracticable due to hardware restrictions. Existing gauges may provide a communications port of some type, but may require connecting the gauge via a communications cable to a master computer. This may occur at the factory during calibration processes, or by the user in order to transfer data at the end of a project; typically at the end of the day. Therefore, the data transfer is thus not real-time.

One or more solutions are needed to address these disadvantages.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein is a system. The system includes a material measurement gauge including a gauge communications module, an adapter configured for communicating with the gauge communications module, the adapter including memory and an adapter communications module, a handheld device operably communicating with the adapter and configured for communicating information, a network in communication with at least one of the adapter and the handheld, and a computing device configured for storing information received from the handheld device and/or the network. A software translator is configured to translate commands from the modern software platform such as a Smartphone or Bluetooth-USB memory adaptor, to the legacy platform on the material measurement gauge. In some cases, the material measurement gauge port is a serial port. In other cases, the port is a printer port.

According to one or more embodiments, the measurement gauge is one of a nuclear density gauge, a gyratory compactor, an asphalt oven, a pavement laboratory device, a pavement field device, an imaging device, or any other gauge or instrument configured for determining the property of a construction material.

According to one or more embodiments, the adapter is a USB configured adapter.

According to one or more embodiments, the adapter includes a GPS or other tracking and/or locating feature.

According to one or more embodiments, the adapter includes Wi Fi, ZigBee, a short range wireless or Bluetooth communication feature.

According to one or more embodiments, the handheld device is a smart phone.

According to one or more embodiments, the network is the cloud, internet, LAN, WI-FI, Cellular, or satellite, Google®, or Google® glasses.

According to one or more embodiments, each component is configured for two-way communication.

According to one or more embodiments, each component is configured at least for one-way communication.

According to one or more embodiments, the adapter is configured to be mechanically attached but removable in one or more embodiments or not removable in one or more additional embodiments to the current port, and is configured with integrated digital, analog, and processing electronics.

According to one or more embodiments, the adapter translates the legacy port to a different port for placement of a variety of memory devices, location devices, and wireless communication devices.

According to one or more embodiments, the adapter is configured for plug and play with the gauge.

According to one or more embodiments, the adapter contains computer program code for enabling the plug and play.

According to one or more embodiments, the adapter receives data from the gauge at the end of a predetermined period of time such as after a measurement, after a group of measurements, a day, or at the end of a project, or simultaneously.

According to one or more embodiments, the adapter is Bluetooth, cellular, LTE, and WIFI® enabled.

According to one or more embodiments, the adapter translates other ports such as the charging port, a printer port, and is waterproof.

According to one or more embodiments the water proof adapter is screwed onto the legacy gauge and has a gasket or o-ring seal.

According to one or more embodiments, the adapter is low profile and neatly fits on the legacy port.

According to one or more embodiments, a method of using the system disclosed herein is provided. The method includes using the measurement gauge to take at least one measurement, operably coupling the adapter with the measurement gauge in order to receive data from the at least one measurement, storing and displaying the data in gauge memory, and further directing the adapter to transmit the data to one of the handheld device and the computing device.

Adapter may include a language translation software program for translating a command initiated from a smart phone to the appropriate command in the library of the gauge For example, the handheld software is written in C and accepts the measurement request from a GUI, this is translated in the adapter to the language of the legacy gauge (such as assembly language command), and adapted to the serial interface for action by the gauge.

According to one or more embodiments, at least one of the elements also tracks location, job performance data, date and time, environmental conditions, and operator information, and further wherein, said information is stored by the adapter and transmitted by the adapter.

According to one or more embodiments, an adapter for use in communicating with a material measurement gauge is provided. The adapter includes a communications module for communicating with the material measurement gauge and a memory for storing computer control code embodying applications and for storing information received from the material measurement gauge.

According to one or more embodiments, the communications module is configured for plug and play with the material measurement gauge based on computer control code.

According to one or more embodiments, the communications module may send data to one of directly to the cloud, directly to a handheld tablet, directly to a phone, directly to a PC, directly to the internet, or combinations above.

According to one or more embodiments, the adapter is configured for communicating with a handheld device.

According to one or more embodiments, the communication occurs either wired or wirelessly, and if wireless, through short range protocol such as Bluetooth®, Zigbee®, WI-FI® and/or CELLULAR.

According to one or more embodiments, the adapter further includes GPS features.

According to one or more embodiments, the GPS feature enables tracking and locating.

According to one or more embodiments, the adapter further includes communication to an external GPS such as located on a smartphone According to one or more embodiments, a kit is provided. The kit includes an adapter configured for communicating with a gauge communications module of a material measurement gauge, the adapter including memory and an adapter communications module and may include a handheld device operably communicating with the adapter and configured for communicating information to a network. The kit also may include the proper application specific program for a SmartPhone or application. This program would include GUI's for controlling the flow of data and commands to the gauge, upload relevant calibration curves or characteristics, store and transfer data. Conversely, much of the processing could take place on the adapter itself. For example in the absence of a Smartphone controller, the adapter could store results and be physically removed for transfer to another computing device. The kit may also include hardware such as a weather proof gasket, fasteners, and mechanical converters to receive the electronic adaptor.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

Figure 1:
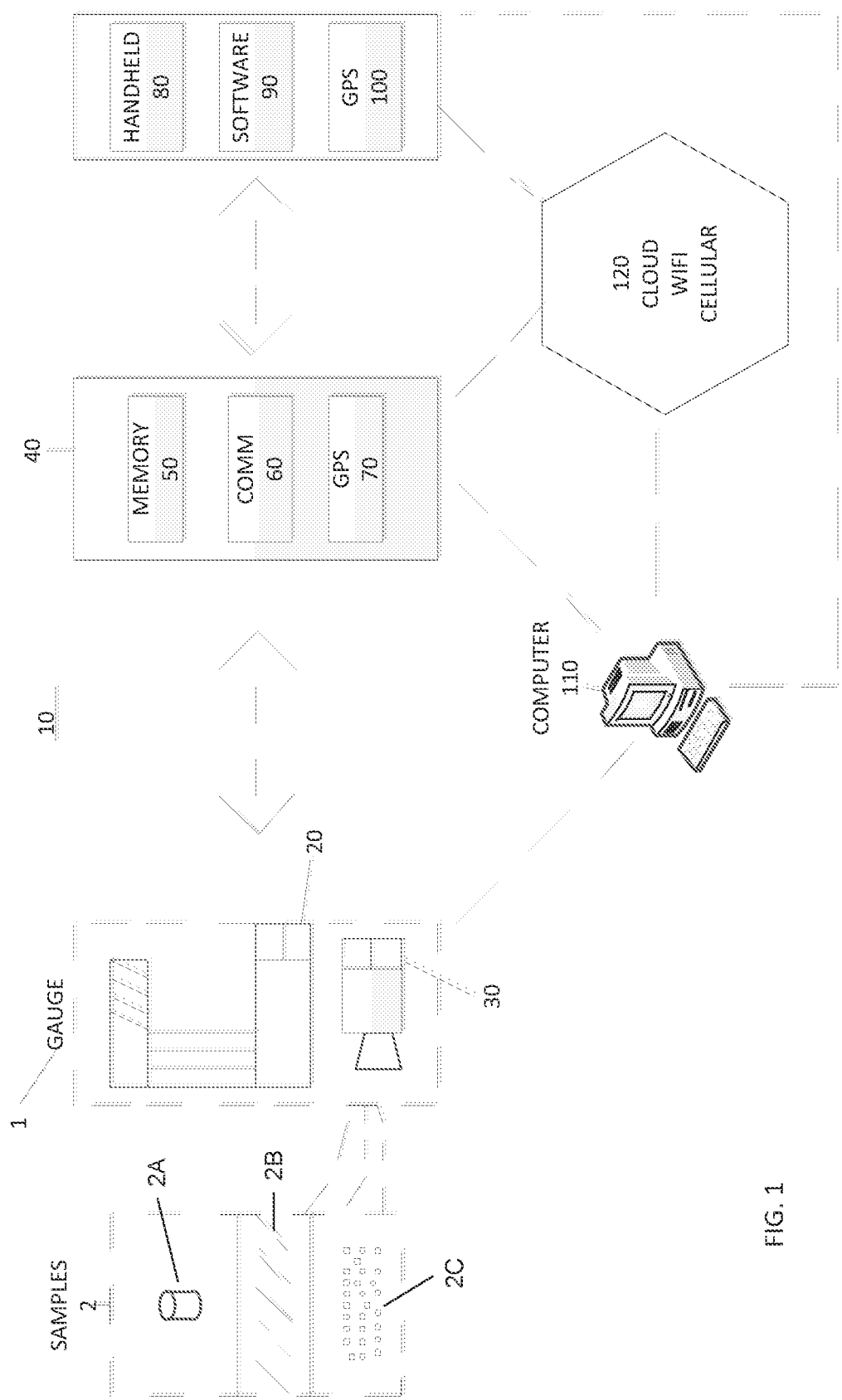
FIG. 1 illustrates a system diagram according to one or more embodiments disclosed herein.

The presently disclosed subject matter is described with specificity to meet statutory requirements. However, the description itself is not intended to limit the scope of this patent. Rattler, the inventor, has contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

A system for determining the density of a paving related material is provided. The measurement results and other identifying or relevant information may be stored in gauge memory. Measurement gauges and other devices used for paving related material have a lengthy service life, however, modern advancements in communication equipment have not been implemented within measurement gauges. This has left users of measurement gauges in the position of deciding between utilizing aged, but useful equipment, and having to manually enter in or transport or otherwise convey measured information, or purchase new equipment with modern communications capabilities. Due to the precision measurements required, effective and useful storage of information, and other considerations, it is desirable to integrate existing (sometimes referred to herein as "legacy equipment") equipment with modern communications capabilities. Heretofore, ability to benefit from features such as wireless control and data transfer has been impractical due to the inability to integrate new hardware and commands into old systems. Furthermore, the modern control commands incorporate new codes making it difficult to select legacy archaic software commands written in different languages and formats. In many legacy cases, there are embedded commands for controlling measurement modes and data transfer that are used in factory calibrations and diagnostics. With the instant inventions disclosed herein, through the use of a software translator, the archaic commands from a legacy system can me remotely controlled with modern electronic hardware through the use of an adaptor and the embedded programming of the translator.

By integrating processors and memory into an external converter or adapter, legacy equipment can meet current standards of data transfer. In one or more embodiments disclosed herein, a gauge may be provided with a serial port in communication with a modern memory device where it is then easily stored on a different computer or uploaded to a database. Data that is transferred from gauge to a database is typically loaded into a spread sheet. Using the legacy protocol along with proper external but local electronic manipulation, methods and apparatuses for converting the signals compatible to modern data transfer techniques are possible. In one or more embodiments, other applications may include two way data and command flow and handshaking. Here, commands can be sent wirelessly from a Smartphone to the data converter, which then communicates with the legacy protocol of the measuring equipment.

The adapter may include a legacy serial port-to-modern protocols such as a USB, serial-to-wireless, serial-to-GPS, serial-to-internet, serial-to-LAN, serial-to-cloud and serial-to-smart phone or pad or combinations of these. The port may not be serial but may be parallel or even a printer port. Typical ports are serial as assumed by the remainder of this disclosure, however, the one or more embodiments disclosed herein may be used in alternate configurations. By using factory legacy commands, not only can data be transferred out of measurement equipment, but commands can be sent over the communication channel to control the equipment, storing results and instantly transferring the results or uploading the results at a later time. In many cases, these commands are previously built into the legacy equipment for calibrating, diagnosing, measuring, and controlling a gauge remotely by wire; but in the factory setting using obsolete methods and programming languages. In this manner, the legacy equipment has a remote control mode used in the factory to control the equipment via serial cable. A preferred method of modern gauge control would include electronics to control a legacy gauge using a smart phone or smart device over a Bluetooth channel. For example, a terminal program could be added to a mobile device such as a cellular phone, commands sent to a gauge set for remote control, and measurement obtained and data transferred to the smart device. The adapter can be configured such that it offers basic service such that the gauge acts as a simple USB host or slave. This USB memory device would be configured to receive project data at the end of a day, or end of a project, or end of a measurement and store it in memory to be transferred physically to a client device such as a computer at any convenient time the user desires. In one or more embodiments, the adapter may include Bluetooth communications channels, and GPS location services. The smart phone internal location services could also be linked or otherwise operably connected to the measurement such that GPS coordinates are obtained from the smart phone each time a remote measurement is initiated, and stored with the measurement results. Other methods of location sensing could involve dead reckoning using accelerometers, gyroscopes, optical gyros and even a first known location reference point. Inclusion of beacon technologies, loran type location algorithms , multiple antenna receiver/transmitters magnetoquasistatic fields with or without GPS, DGPS or AGPS assistance could be implemented.

FIG. 1 shows system 10 including a sample 2, legacy gauge 1, and legacy electronics 20 which may include a serial connector, level shifters, analog and digital electronics for obtaining a measurement. Sample 2 may include any type of construction related sample, and, in one or more embodiments, may include an asphalt or pavement core, a road surface, asphalt, concrete, an aggregate, as illustrated, or any other construction related equipment. As illustrated, a core 2A, aggregate 2B, roadway 2C, or any other construction material may be provided for being measured. Legacy gauge 1 may include a nuclear density gauge 30, an imaging device, an electromagnetic gauge such as a Pavetracker, asphalt content gauge as the Troxler NTO or neutron based 3241, Gyratory compactor, or any other construction related gauge configured for taking a measurement of a construction related sample. The gauge 1 may include electronics 20 provided for communication and programs being executed thereon.

An adapter 40 may be provided that attaches to the gauge 1 via communication with electronics 20. This adapter may be a parasitic board that attaches to gauge 1 and 20. Memory 50 may be provided that includes programming and storage of information provided by the legacy gauge 1. Memory 50 may be any appropriately configured type of memory, including FLASH memory, ROM, RAM, SSD, and the like.

The adapter 40 may include a mechanical adapter from the existing serial port to a USB port or other communications module. The USB port could accept any device including a memory stick, a communications module 60 such as blue-tooth®, and a GPS module 70. Adapter 40 may contain a processor or programmable integrated circuit which could contain controlling programs and codes and be of any interface such as fire wire, DB9 serial or parallel or printer port. Adapter 40 can then be incorporated to transfer stored data from legacy gauge 1 to a computing device 110 by physically storing data onto adapter memory 50 and inserting it into computing device 110. Adapter 40 could be used in a Bluetooth mode in communication module 60 to wirelessly transfer data to a handheld device, such as a smart phone 80 or Google® Glasses or visual aids. Smart phone 80 could contain application software 90 and transfer data to other computers 110 or the cloud 120. Cloud 120 may include any appropriately configured network, including the internet, LAN, WI-FI® and cellular.

Smart phone 80 may also include applications executing thereon to control gauge 1. In this mode, smartphone 80 could communicate and send remote commands directly to gauge 1 via the communication channel 60 using Bluetooth or other wireless technology.

Figure 2:
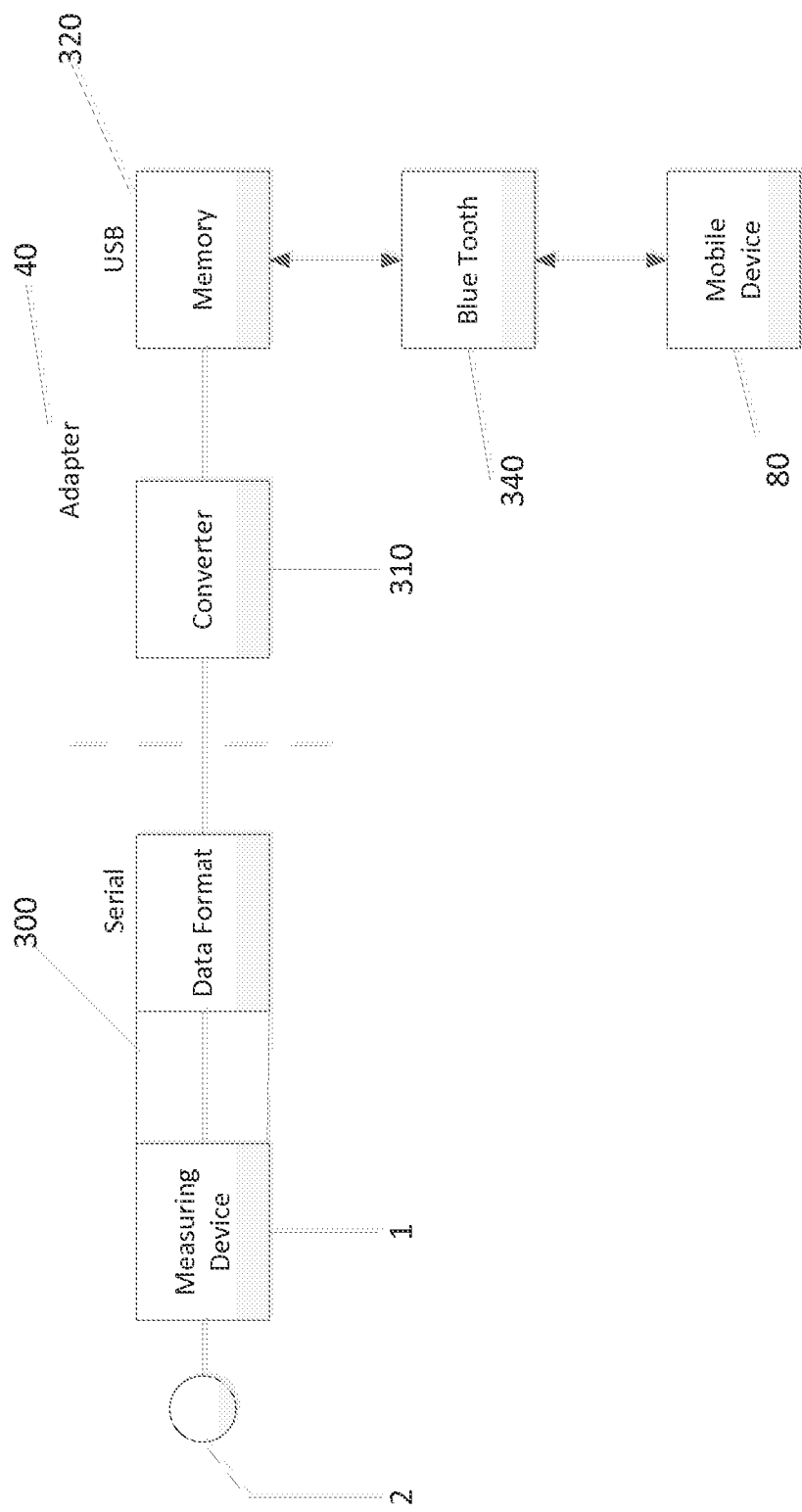
FIG. 2 illustrates a system diagram according to one or more embodiments disclosed herein.

FIG. 2 shows another form of the adapter 40 where the measuring device 1 is monitoring a sample 2 and submitting data to the serial or parallel formats 300. The adapter 40 is external to the gauge and may consist of a level shifter, processing unit, PIC, FPGA converter 310 and a USB memory device 320 in communication with a wireless data transfer device such as a Bluetooth communications module 340. Communications protocol can be Bluetooth® to communicate with smartphone/mobile device 80.

Figure 3:
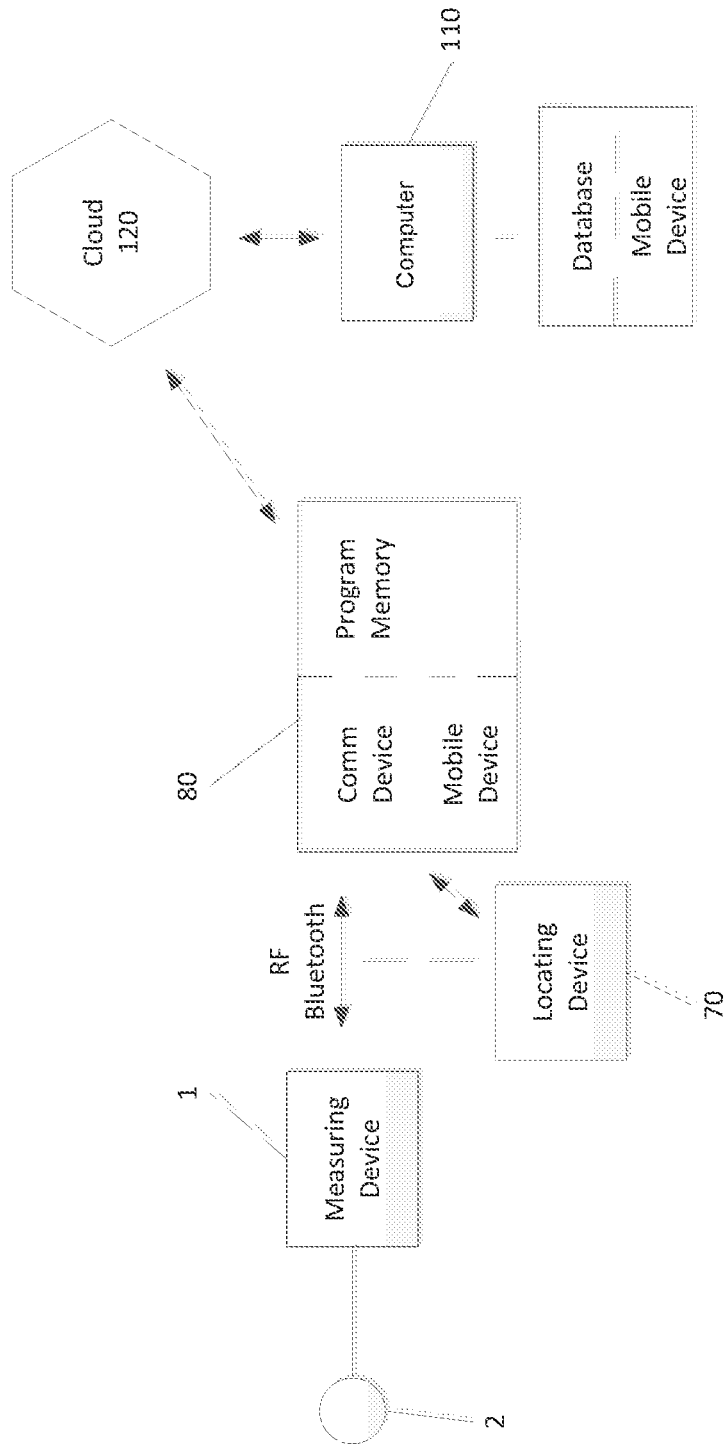
FIG. 3 illustrates a system diagram according to one or more embodiments disclosed herein.

FIG. 3 shows measuring device 1 with a GPS or locating device 70 in operation in the gauge 1. Newer equipment may already have GPS integrated into measurement device as an option. Newer equipment such as the Troxler® 3440 Plus gauge may already be capable of hosting a USB memory device, with the 3440 Plus gauge being described in U.S. Pat. No. 8,164,048 which is incorporated by reference in its entirety. However as described herein, the USB port is capable of hosting a wireless communication module which allows the gauge 1 to be controlled by an outside remote computer such as a smart phone 80, or simply be used as a memory port. Remote computer device or smart phone 80 may include its own GPS locating device whereby location data is initiated along with control of a measurement to gauge 1 in its serial port. Computer device 80 may include application software, control programs graphical user interfaces and plotting routines. GPS may also be part of the add-on module of the adapter 40, though it is not illustrated in FIG. 3.

Figure 4:
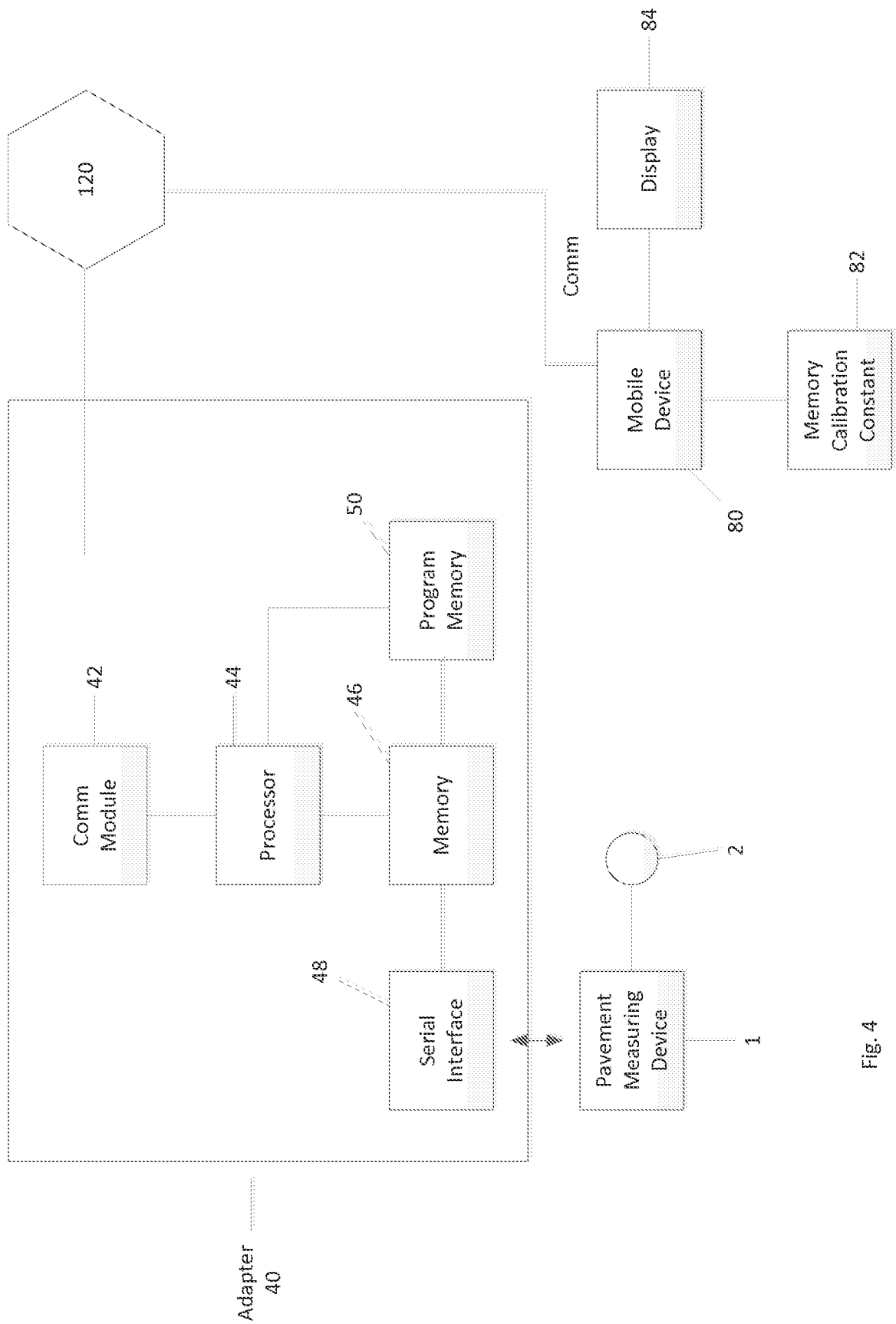
FIG. 4 illustrates a system diagram according to one or more embodiments disclosed herein.

FIG. 4 shows adapter 40 as containing a communications module 42, microprocessor or PIC 44, memory 46, serial interface 48, and programmable memory 50 as well as data storage memory. Adapter 40 is Bluetooth connected with smart phone 80 which contains capability to upload calibration constants or data and diagnostic results from measuring device 1. Smart phone 80 can display measured values of sample 2 including moisture % M and density in PCF or Kg/m$^3$. The smart phone/mobile device 80 may include calibration constants in the memory 82 of the phone and have a display screen 84 for viewing by an operator. Network 120 is also illustrated. Calibration constants may be obtained by downloading from gauge, remote server, or manually added.

Figure 5:
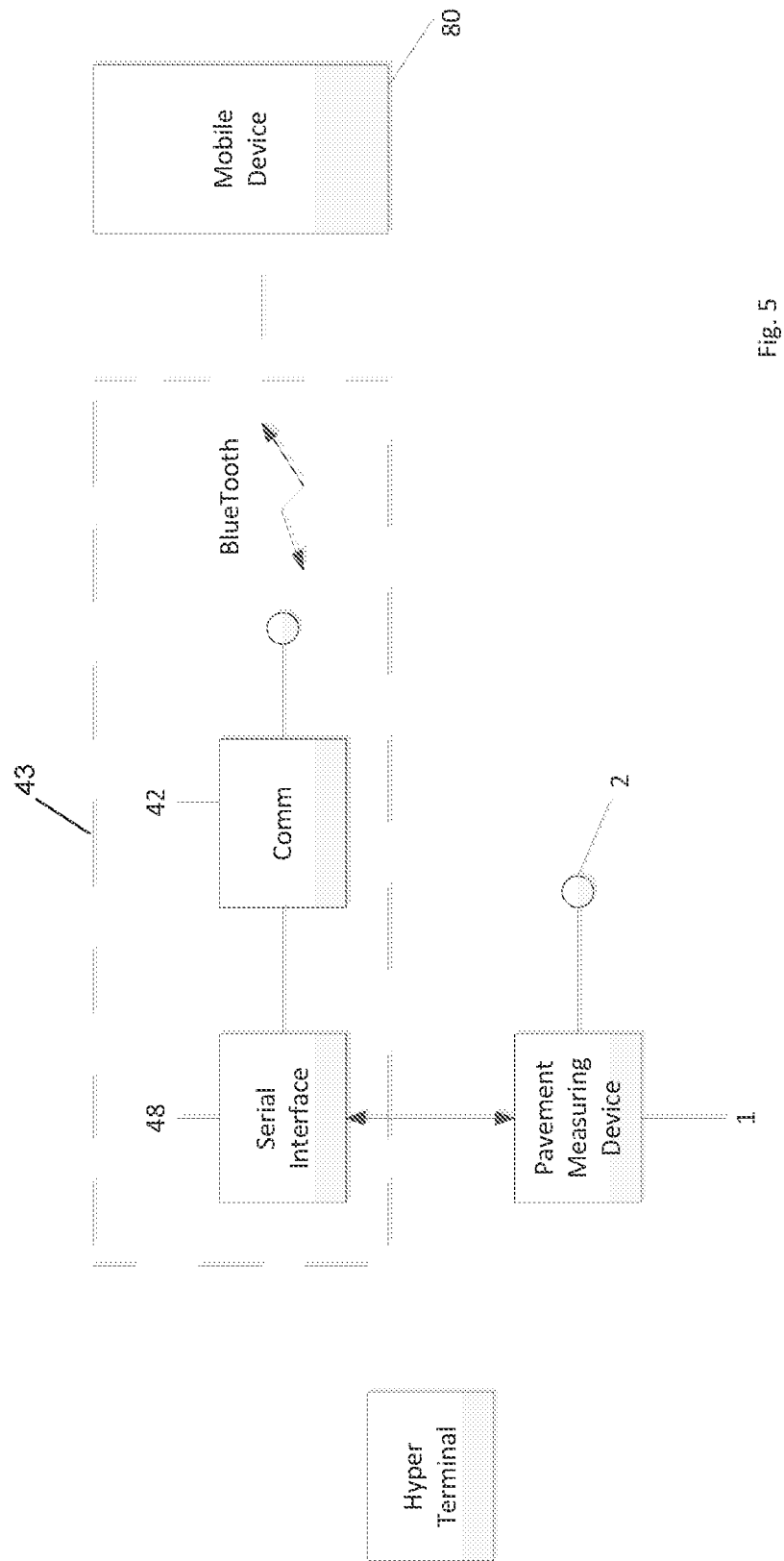
FIG. 5 illustrates a system diagram according to one or more embodiments disclosed herein.

FIG. 5 shows measuring device 1 in communication with adapter 43 consisting of an interface 48 and a communication module 42 remotely in communication with smart phone/mobile device 80.

Figure 6:
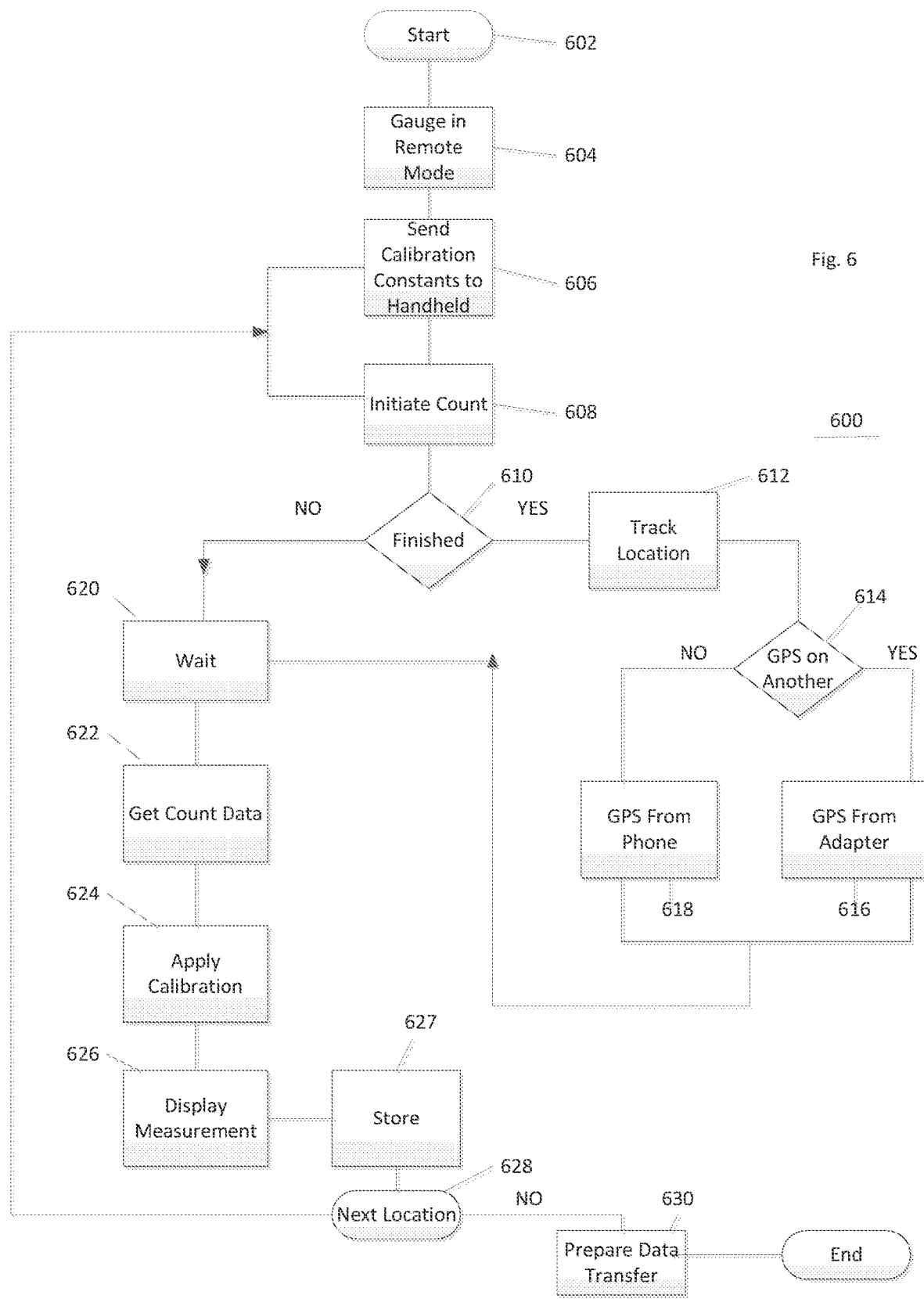
FIG. 6 illustrates a flow chart according to one or more embodiments disclosed herein.

FIG. 6 is a flow chart showing a method 600 for controlling a gauge using a remote device such as a smart phone. The legacy gauges have many commands that can control the state of the measurement gauge 1 in the factory. This adapter will allow for field smart phone control or smart watch control, or smart glass control of gauges using and converting the commands. For example, commands such as "Take a count" already exist in the factory for calibrating and diagnosing the gauges. Here, the gauge is put into remote control and through a PC and a wired connection can be addressed to take counts, go to idle, turn gauge off, read standard count, read battery voltage, set count time, set rod depth, receive calibration constants, display a message on the user interface of the gauge 1, send calibration constants, and perform diagnostics. For example, after entering remote control the command &#TAC instructs the gauge to start a measurement. By reading the count time &#RCT the gauge instructs the software application to wait 4 minutes plus a few seconds so that it can report the measured raw data. By uploading the calibration constants to the smart application, the raw data is applied to the proper calibration constants and the smart phone can display the corrected density and moisture results. Typical data formats may include raw, corrected and formatted. Corrected data would be after applying a calibration to the results. Formatted data might include the units such as PCF or Kg/m$^3$. Furthermore, if GPS is not on the gauge 1, the smart phone can attach its GPS location or coordinate data at or about at the time of the count initiation. The location data can be absolute or relative.

The method 600 includes starting the measurement process 602. The method 600 includes determining (604) that the gauge 1 is in remote mode. As used herein, the gauge is in remote mode 604 means gauge is ready to accept remote commands and expecting a legacy wire connected to the internal port; but instead will receive commands from a wireless adaptor and software translator. In some cases, remote mode is entered by an administrator keying in a code on the gauge keypad. Once mode is enabled, gauge awaits further commands from serial port. Otherwise, command and control is from the keypad. The method 600 may include sending (606) calibration constants to the handheld/mobile device. The calibration constants can be transferred any time prior to displaying or calculating the measurement results. In this flow chart of FIG. 6, the transfer of calibration characteristics precedes the measurement count. In one or more embodiments, this could be transferred after the raw data count. The calibration constants or characteristics could also be received into either the adapter memory, or the handheld smart device memory; and received from the gauge itself or even from a remote server. In some cases, the calibration coefficients could be manually typed into the smart device. The calibration characteristics could be received instantly when needed, or preloaded at some previous time. The calibration characteristics only need to be loaded once and not every time the gauge is used. The calibration constants typically are good for at least a year before the mandatory calibration procedure is performed. The method 600 may include initiating (608) a count (for nuclear gauges, a count means counting analog pulses using a Geiger counter or scintillation detector or the like). The method 600 includes determining (610) whether the count is finished. If finished, then the location is tracked 612. The location may be tracked by the locating device 70 or any GPS device or locating device disclosed herein. If the GPS is on the adapter, then location is read (616) from the adapter 40. At step 614, if the GPS is not on the adapter, the mobile device 80 is communicating with the gauge 1 and records (618) the location of the mobile device 80, which is consistent with the location of the gauge 1 at the time of measurement.

If the count is not finished, the method 600 includes waiting 620. At this time, location measurements are provided by either of step 616 or 618. The method 600 may include getting data count 622. The method 600 may include applying calibration to the counts 624. Calibration may include providing one or more calibration constants to determine density, moisture, or other measurements thereof. The method 600 may include displaying measurements 626. The measurements may be displayed on the gauge 1 or on the mobile device 80. The measurements are then stored 627 in one or more memories. The memory may be on the gauge 1, the mobile device 80, or both. The method 600 may include moving the gauge 1 to the next location 628 if there is a next location. If there is a next location, the counts are initiated 608 in a loop on the flowchart, and wait for the next command from the user. If there is not a next location, data may be transferred 630 or the file closed. The data transfer may be in the cloud 120 to an external server.

There are many ways that these features can be applied to gauge 1. For example, a smart USB device such as in FIG. 5 contains memory and a microprocessor. This would allow calibration constants to reside on the adapter 40 which is physically with the gauge, and the adapter could also have its own GPS module and battery supply so that commands could at least be partially submitted to the gauge via the adapter.

Adapter 40 can also consist of a USB memory and programmable PIC that would allow for a GPS chip set such as the SIRF family or products from Qualcomm such as its CDMA cellular links or Snapdragon location technology to be included in the adapter, or a GPS, AGPS, DGPS interface to accept an after market GPS directly attached to the gauge and read by the adapter 40. Other cellular links would include GSM, TDMA, FDMA etc.

Figure 8:
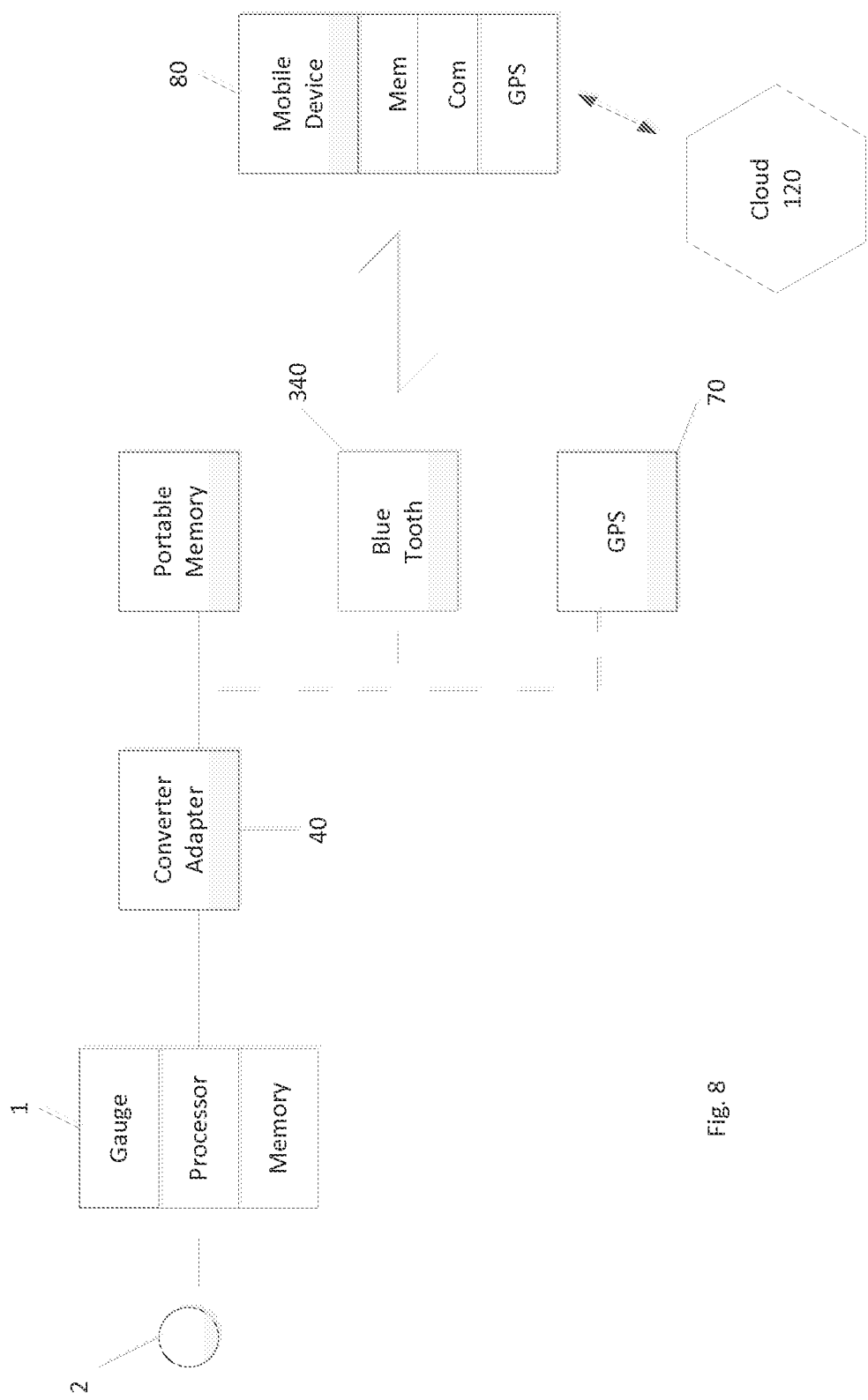
FIG. 8 illustrates a system diagram according to one or more embodiments disclosed herein.

Particular applications for the Smartphone 80 could mimic the terminal programs such as HyperTerminal and Tera Terminal. These applications could be written for iPhones or androids. A simple application software example is terminal BT FIG. 8 shows the gauge 1 transferring to a serial port and then external to the gauge 1 a converter and or adapter 40 which can be connected to a memory device such as a USB, a wireless device such as Bluetooth 340, and a GPS location device. These reside local to the gauge. One or a multiple amount of devices can be attached to the gauge port in this fashion. The wireless device can further communicate with a smart device such as a smart phone which can connect to the cloud, other smart device, WiFi, server, PC twitter, FB, external media. The smart device may further manage memory, processor, and GPS which is not local to the gauge, but is a short distance from it or spaced apart.

Figure 7:
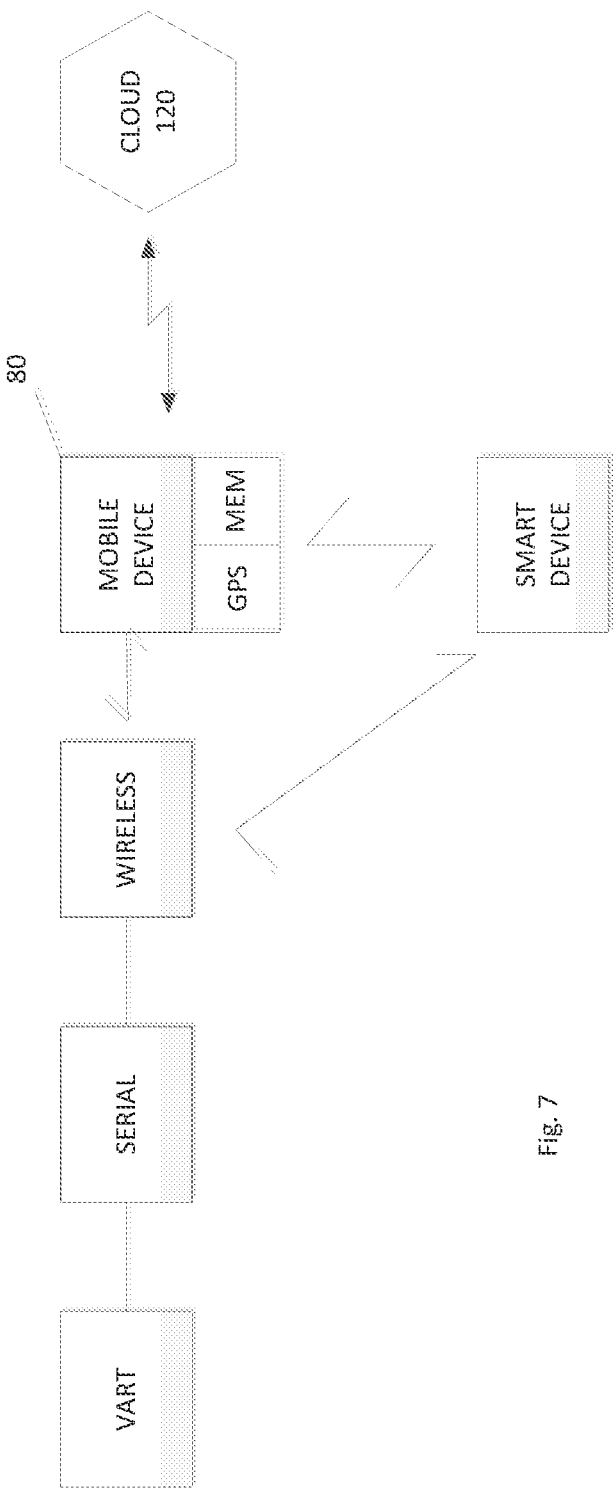
FIG. 7 illustrates a system diagram according to one or more embodiments disclosed herein.

FIG. 8 is similar to FIG. 7 but uses the serial port for communication to the memory, Bluetooth, or GPS. Multiple smart devices can also be configured for communication to the older equipment.

Figure 9:
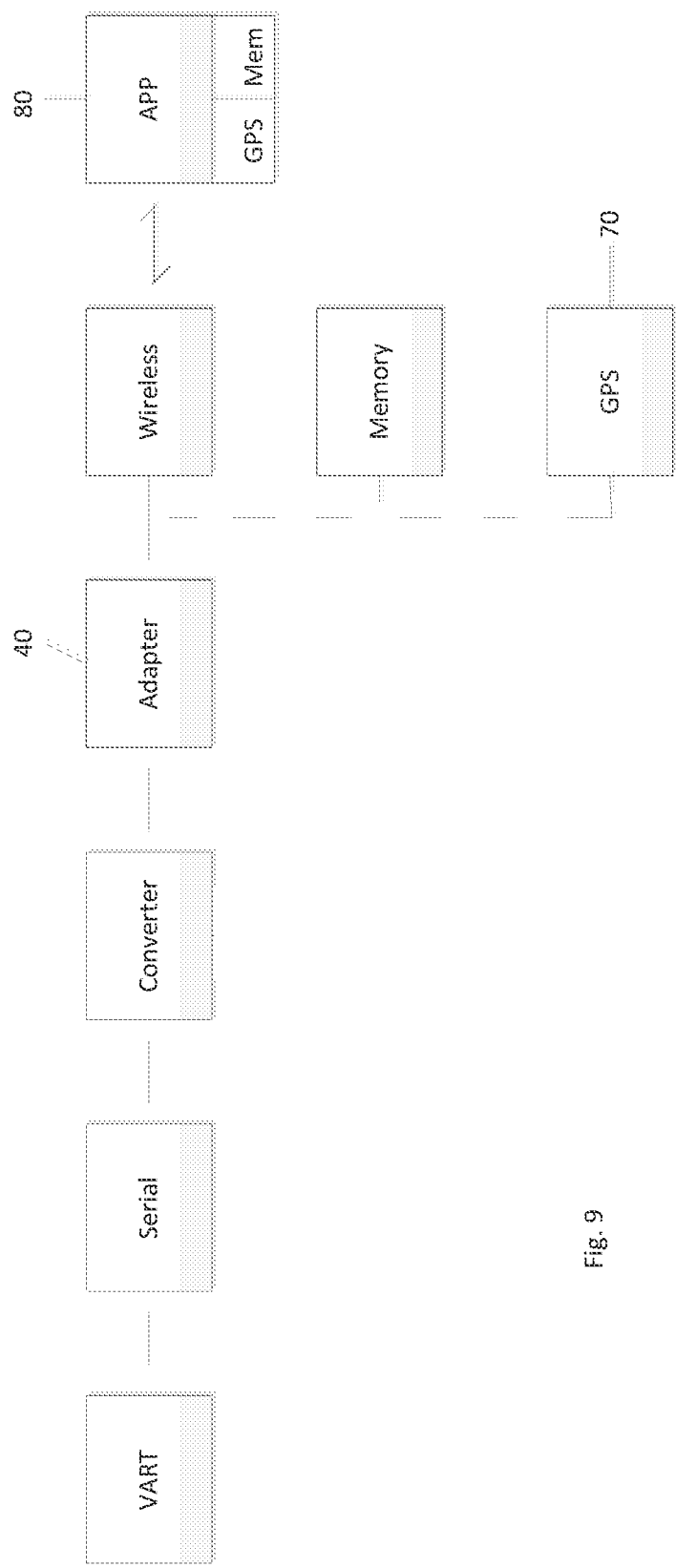
FIG. 9 illustrates a system diagram according to one or more embodiments disclosed herein.

FIG. 9 incorporates an adapter or converter when the hardware accessories such as GPS, wireless, or memory are all optional.

Figure 10:
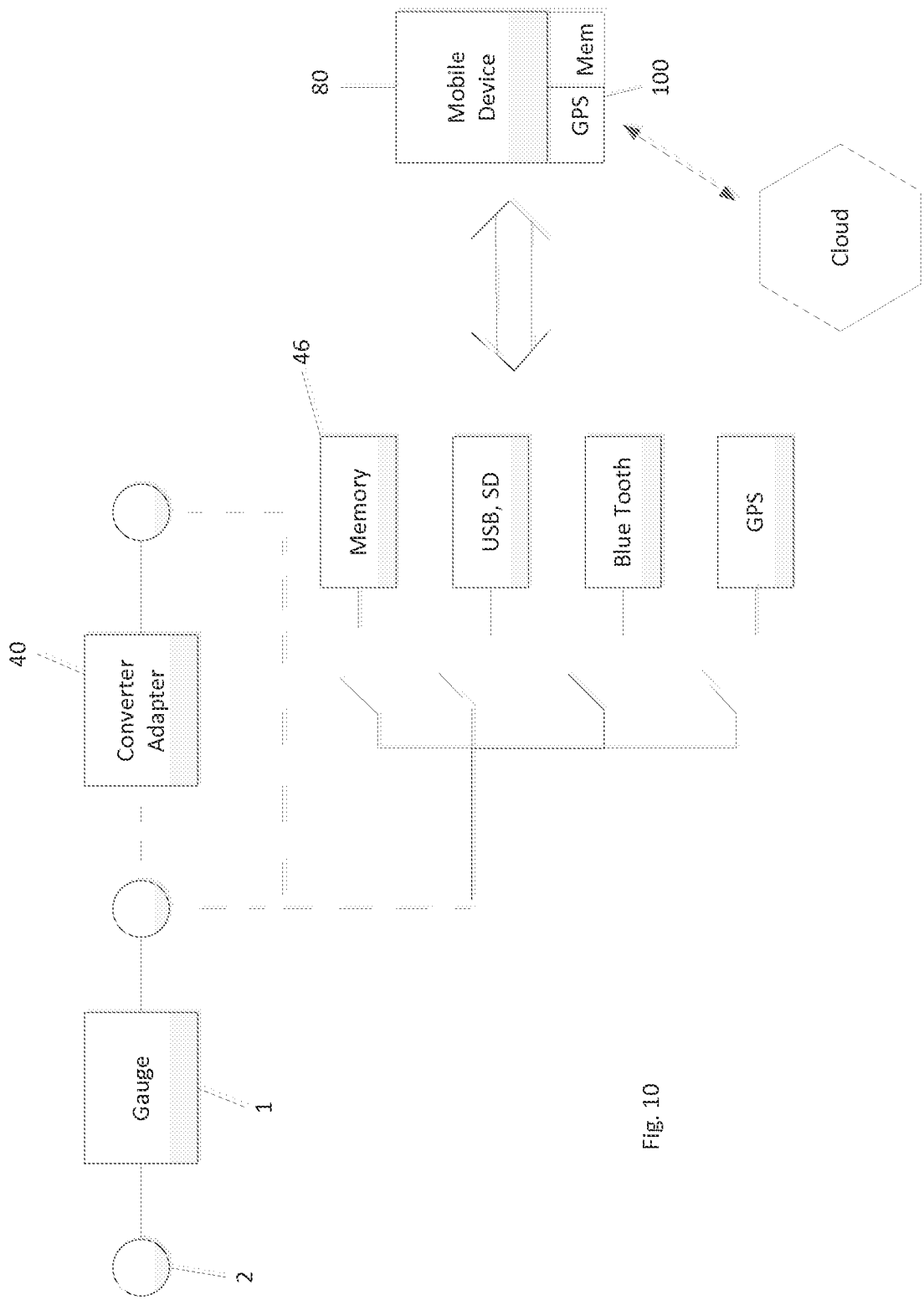
FIG. 10 illustrates a system diagram according to one or more embodiments disclosed herein.

FIG. 10 shows that an adapter or converter 40 may or may not be necessary for the add-on options. These options may be attached as a kit, or configured at the factory. Here the accessories are optional and switchable from a dip switch, or software switch.

Figure 11:
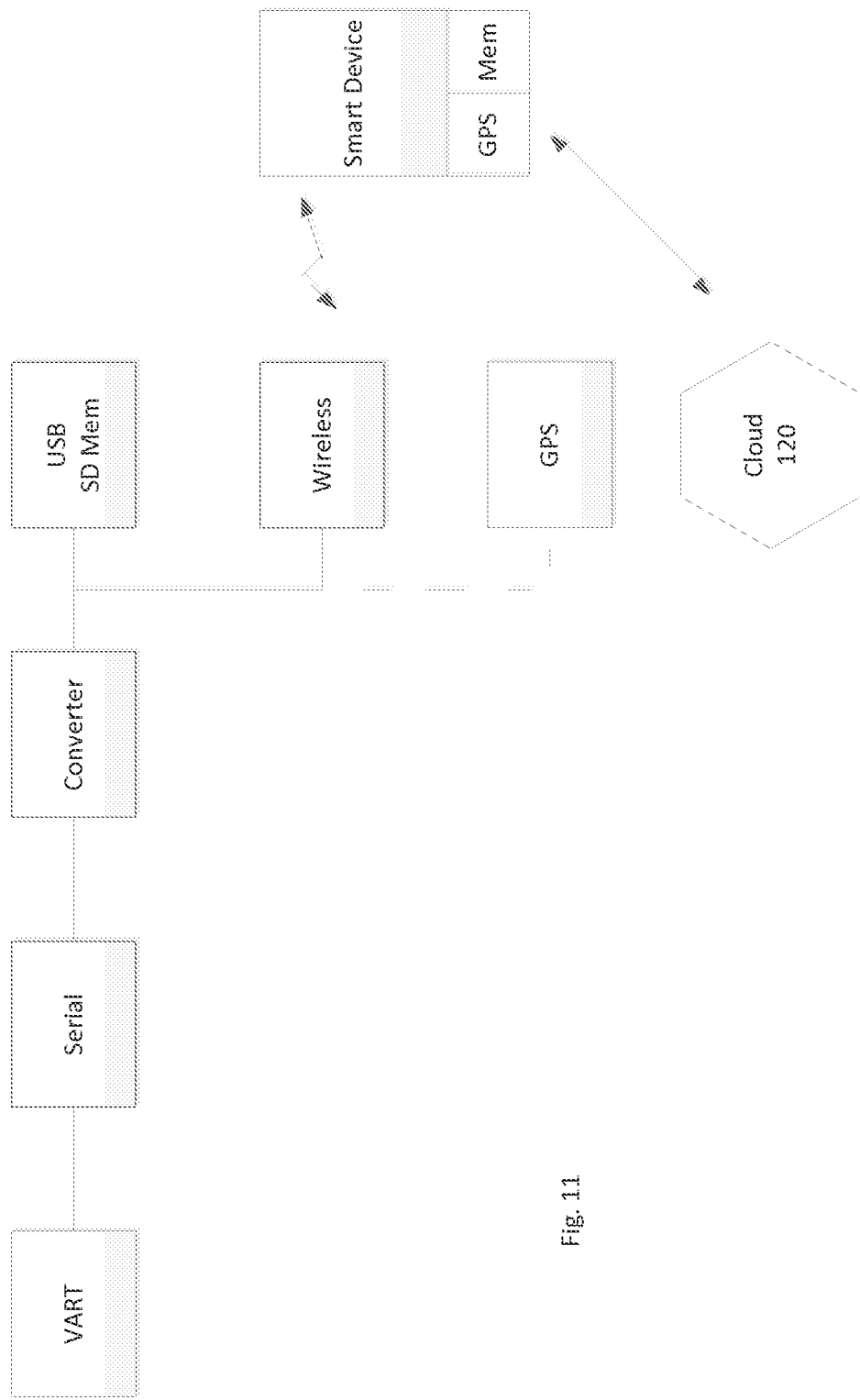
FIG. 11 illustrates a system diagram according to one or more embodiments disclosed herein.

FIG. 11 shows a gauge where the factory calibration port is connected directly to a wireless Bluetooth serial port which in turn can communicate with a Smartphone application software, multiple software platforms, the cloud, other smart device, WiFi, server, PC, or twitter. Many communication platforms are mentioned in U.S. Pat. Nos. 7,848,905 and 8,112,242, 8,164,048, incorporated by reference herein in their entirety.

Figure 12:
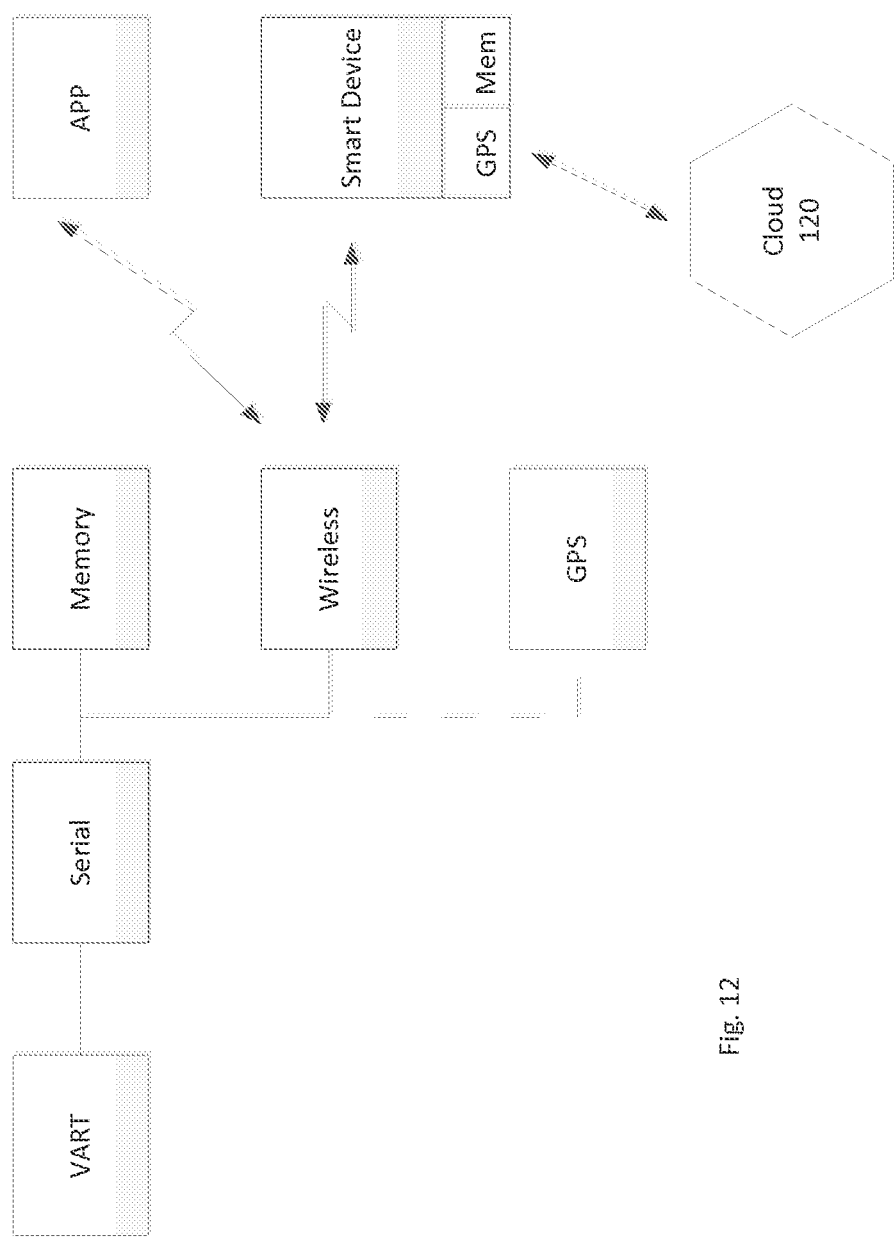
FIG. 12 illustrates a system diagram according to one or more embodiments disclosed herein.

FIG. 12 shows the gauge in measurement mode measuring a sample directly, using a hand portable measurement system with site or position selectable "spot" measurement approach/techniques. The gauge contains memory and a microprocessor, but is typically taken to the office and downloaded using a PC and a terminal program. Location services are not available on these older legacy gauges. However, by attaching an adapter (kit) to the serial port of the gauge, we can add a portable memory such as a USB stick, Bluetooth, and GPS. These wireless Bluetooth devices can communicate with the Smartphone android, or iphone, or Google Glass which can communicate with the outside world such as the cloud, cell network, other smart device, WiFi, server, PC twitter. The GPS is shown on the adapter located on the gauge, otherwise, when a measurement is initiated by the smart phone, the GPS of the smart phone can be used to obtain and store location.

Figure 13:
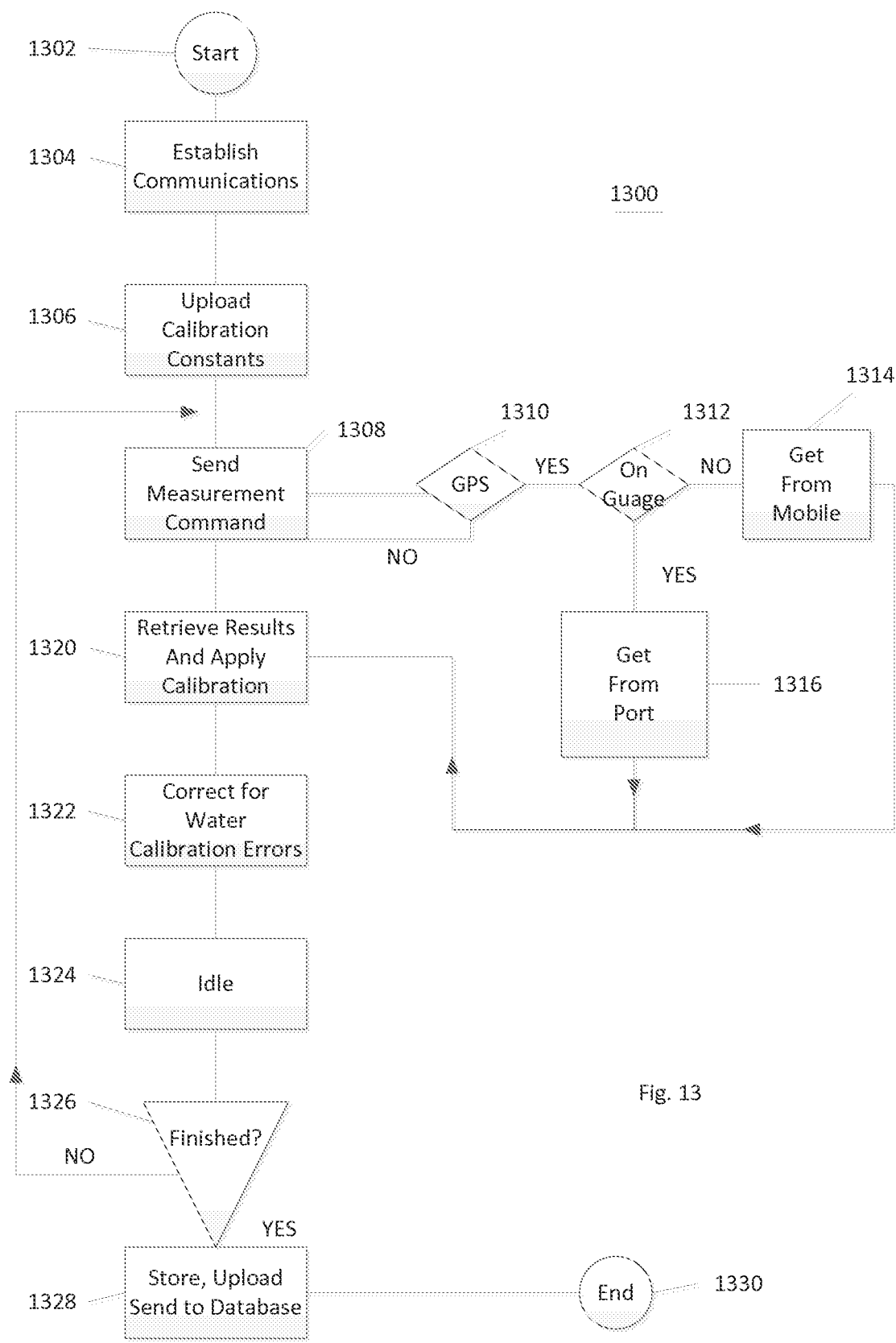
FIG. 13 illustrates a flow chart according to one or more embodiments disclosed herein.

FIG. 13 is a flow chart of a smart phone application controlling a legacy gauge using the serial port of the gauge. One or more methods 1300 are provided. The method 1300 may include starting 1302. The method 1300 may include establishing communications 1304 between the mobile device 80 and the gauge 1. If GPS is not on the gauge 1, it is close by as the smart phone has a GPS whose coordinates are obtained at or about at the same time and location as the measurement process. At the end, the data has been transferred to the smart phone and can be uploaded to the cloud, internet, server, twitter, facebook, database, home base, using typical communications channels like Lan, WiFi, cellular links such as 3G, 4G, and LTE.

The method 1300 may include at step 1306 uploading or downloading calibration constants from the mobile device 80 to the gauge 1 or from the gauge 1 to the mobile device. In this manner, calibration constants can be provided in real time via the mobile device 80 that accesses the same from the cloud 120 or other network. The mobile device 80 then directs the gauge to begin taking measurements 1308. Upon completion of measurements 1308, if at step 1310 the gauge 1 is equipped with GPS, the location is received from the tracking module on the gauge 1316. If at step 1312 GPS or other tracking is not on the gauge, then the location is retrieved from the mobile device 1314. The method 1300 then includes retrieving results 1320 from the gauge 1 and applying calibration using the calibration constants. The method 1300 may further include correcting for water calibration errors 1322 and correcting other measurement data for the presence of water. For example, calculating dry density from wet density, or dry modulus from wet modulus. If the method 1300 detects idleness (1324) of the gauge and/or measurements, the method 1300 may determine (1326) that the measurements are finished. If not finished, then the method 1300 loops back to the measurement command 1308 and may wait for the user to press "measure" on the hand held which is communicated to the gauge through the adapter. If finished, the measurement data is stored and uploaded to a database 1328. The method 1300 finishes and may include powering down the gauge at that time 1330. Note that GPS or "location like" coordinates may be obtained any time during other measurement, before, after, or during the act of measuring; as long as the location remains the same.

In 1306, calibration constants are uploaded. In some cases, corrected data can be transmitted by the gauge so calibration constants may not be necessary. Otherwise, adaptor 40, translator, or Smartphone 80 can accept the raw data and apply the appropriate calibration curves. Likewise, the hand portable or RF linked device can actually be used to calibrate the gauge and calculate its own calibration constants. Here the remote hand held or tablet accepts raw data from known materials and fits a curve using at least one standard, or multiple standards. These standards such as Magnesium, Aluminum and Magnesium/Aluminum have known properties. The algorithm for curve fitting and determining the calibration coefficients for the appropriate states of the gauge are stored in the smart device, calculated by the smart device and translated via the adapter to the legacy gauge if desired.

Bluetooth Adapter:

Upgrading with this adapter 40 allows for a portable expandable system. Typical use for the basic adapter would be that a user obtains their project measurements and stores the data on the gauge in the usual way. The adapter 40 is placed on the serial port of the legacy gauge 1 and the gauge 1, acting as a host, sends the project data directly to the USB. The USB is then removed and placed on a computer or computer network for transfer of data. This USB is upgradable and can also allow for wireless communication. In this mode, the data can be uploaded to the wireless data transfer module and can be sent by RF to the client computer, Smartphone, laptop, LAN, tablet, or cloud. The smartphone/mobile device 80 could also be an intermediate step where the data is transferred to the phone, and the phone links with a cellular network for further transferring of files or connecting to the internet, WiFi, or cloud. The RF file transfer of the gauge adapter 40 could also be WiFi as well or any of the IEEE 802.11 type protocols.

A further upgrade to the adapter 40 would allow for commands to be downloaded to the gauge 1 as well as information to be transferred in either direction between the gauge 1 and a smart phone 80. One possible approach would follow method 600 of FIG. 6 where:

1) Gauge is placed in remote control mode via keypad in step 604. A predetermined key sequence on the gauge may be required.
2) Calibration constants are transferred to the memory on the adapter 40 or smart phone in step 606.
3) Gauge 1 is set up for the proper count time, mode, source depth or backscatter, and diagnostics (optional) read.
4) Standard counts are transferred.
(5) If no standard count found, then the user is prompted via Smartphone 80 or gauge user display to obtain a standard count.
6) User is prompted to obtain a measurement count by GUI on smart device.
7) Measurement count is obtained and transferred to adapter 40 or Smartphone 80.
8) On Smartphone 80 or adapter 40, the calibration constants are applied
9) Corrected results displayed and stored in adapter 40 or Smartphone 80.
10) Data recorded and prepared to be sent to spreadsheets or analysis programs such as plotting routines.

ILLUSTRATIVE EXAMPLES

3440 Components
Serial Port

The serial port, such as that which is shown in FIGS. 9, 11, and 12 may contain a logic level of 1 (+5 volts) on any input of the RS-232 driver U5, will produce −5 volts on the corresponding output. A logic level of 0 (0 volts) on an input of U5 will produce a 5-volts output. A MC145406 chip may be employed. The adaptor translates the commands to the legacy gauge at the proper logic levels which may be much different than the Bluetooth or wireless voltage levels.

A "null modem" or "straight" cable is used to connect the 3440 gauge to a computer or printer.

As a result, one of the main features of the one or more inventions disclosed herein is the transferring of timing, voltage levels, and protocol from the old legacy system 1 to the adapter 40.

In one example, the legacy gauge 1 can send project data with density and moisture data, but it cannot be queried for a single reading and send moisture and density data.

For certain legacy gauges, if the operator wants to take counts "automatically", the operator has to start an extended test from the keypad. In that mode, the gauge sends the results to the serial port. After it sends, it pauses, then checks to see if the port is still open. If it isn't, it "freezes" until the port opens up again. By shutting down the port after a count is acquired by the computer, then opening it up again after the gauge has been moved to the next measurement position allows for automatic gauge calibration or a continuous measurement sequence.

If the operator wants to send constants to the gauge, the operator has to put the gauge 1 in calibration constants mode from the keypad. The gauge 1 then checks to see if the serial port is open. If it isn't open, the operator is prompted to enter the constants manually. If the port is open, then it accepts data that are sent to the gauge through the serial port. Once it gets all of the data, it stores them and jumps out of that model.

Figure 14:
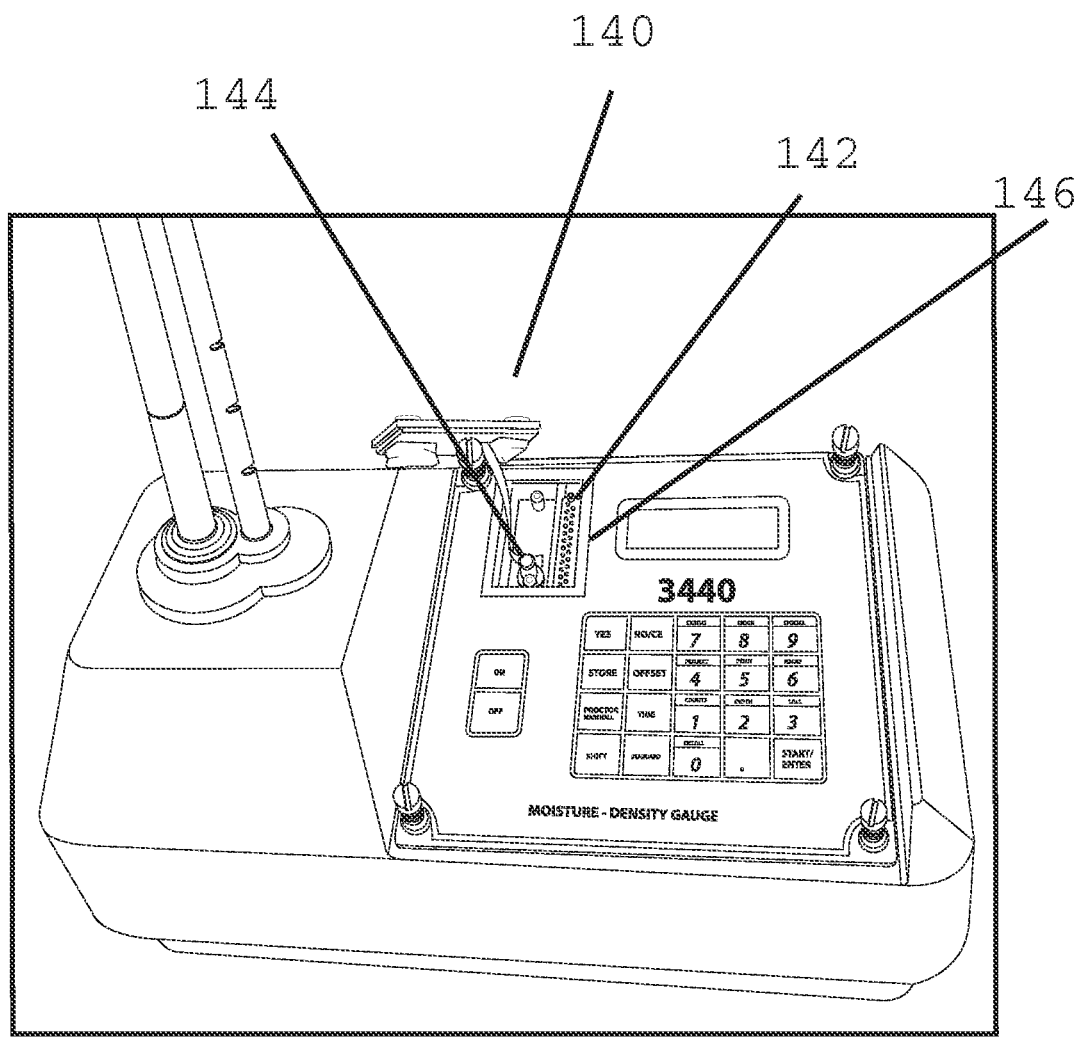
FIG. 14 illustrates a legacy gauge having a communications port exposed according to one or more embodiments disclosed herein.

FIG. 14 illustrates a nuclear measurement gauge having an existing communications port being exposed by removal of a cover. The existing port picture shows the recessed portion 140 on the legacy gauge that contains the serial port 142 with a null modem connector, and the charger port 144. In one or more embodiments, the portion 146 around the recessed port is where an o-ring, rubber seal, or other resiliently engageable seal would be placed when the adapter is fastened to the port.

Figure 15:
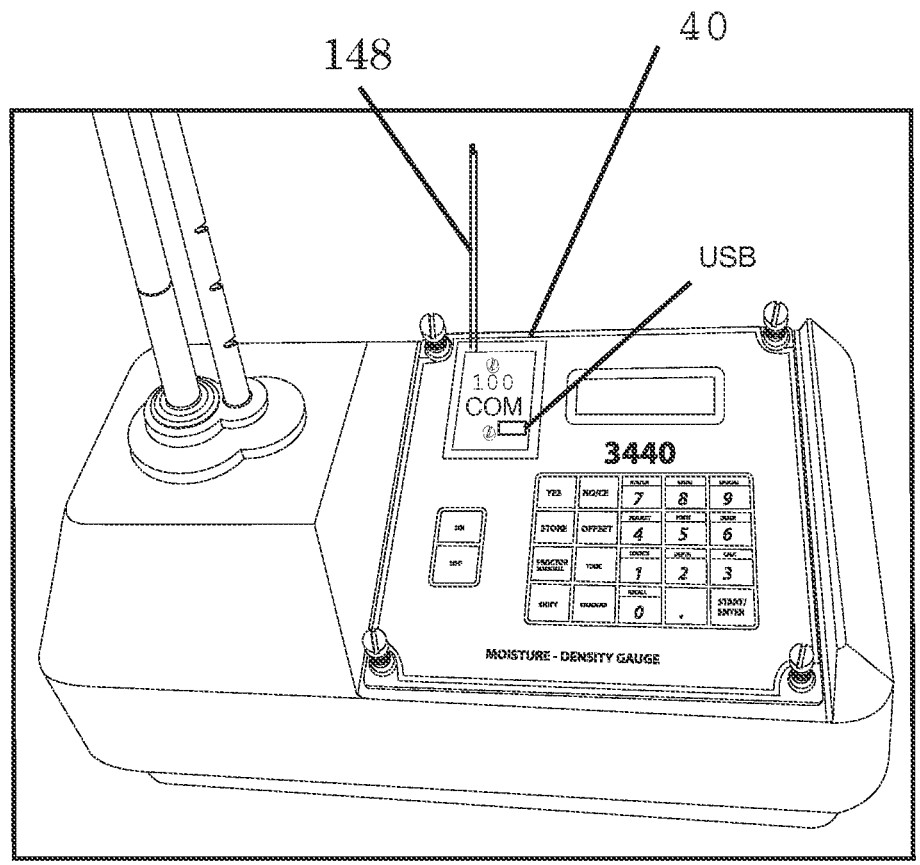
FIG. 15 illustrates an adapter installed within the communications port of FIG. 14 according to one or more embodiments disclosed herein.

FIG. 15 illustrates an overview picture that shows a cover for adapter 40 that has been fastened to the recessed port, internally connecting to the charger, and serial port. The charger port is reproduced on the outside of the adapter, while internally, the serial port is plugged into the adapter. The adapter 40 may contain all electronics as already described herein, such as the FTDI chip, power rails, conditioning, memory, processor, and batteries. In other words, the adapter 40 has a likewise connector configured for communicatively coupling to each input/output connector found within the recessed portion 140. Adapter 40 may contain an antenna 148 and includes location modules, communications modules, and a USB or other I/O communications port. The USB may be connected to a portable external storage memory. In this manner, data can be stored on the external storage memory through a job period, such as a day, and then communicated via a flash drive or the like.

In one or more embodiments, the adapter 40 is powered by the gauge's internal battery supply, via the serial port on the gauge. In these one or more embodiments, batteries and/or an external power source would not be required. Battery power may be added to adapter as necessary.

In one or more embodiments, an adaptor configured for being received by an existing cmnixtunications port of a material density gauge is disclosed herein. The adaptor includes one or more communications members configured for being communicatively coupled with the existing communications port of the material density gauge. The adaptor may include batteries for powering the communications aspect of the adaptor or the adaptor may be configured for parasitic operation from electronics of the material density gauge.

The adaptor may be configured such that the adaptor is powered on only when a measurement is taken. In this embodiment, the adaptor is not a parasitic drain except when measurements are taken, thus conserving battery power for the measurement gauge. Thus, one or more methods may be provided that include taking a measurement with the measurement gauge, in response to the measurement being taken, the adaptor powering on, and the method also including transmitting measurement data along with additional data such as location, time of measurement, operator, and the like through the network. Immediately after transmitting the measurement, the adaptor can either power down entirely, or power down the communications aspects that likely impact battery life.

The adapter is also illustrated with a bluetooth or other communications antenna, GPS, USB memory stick.

Figure 16:
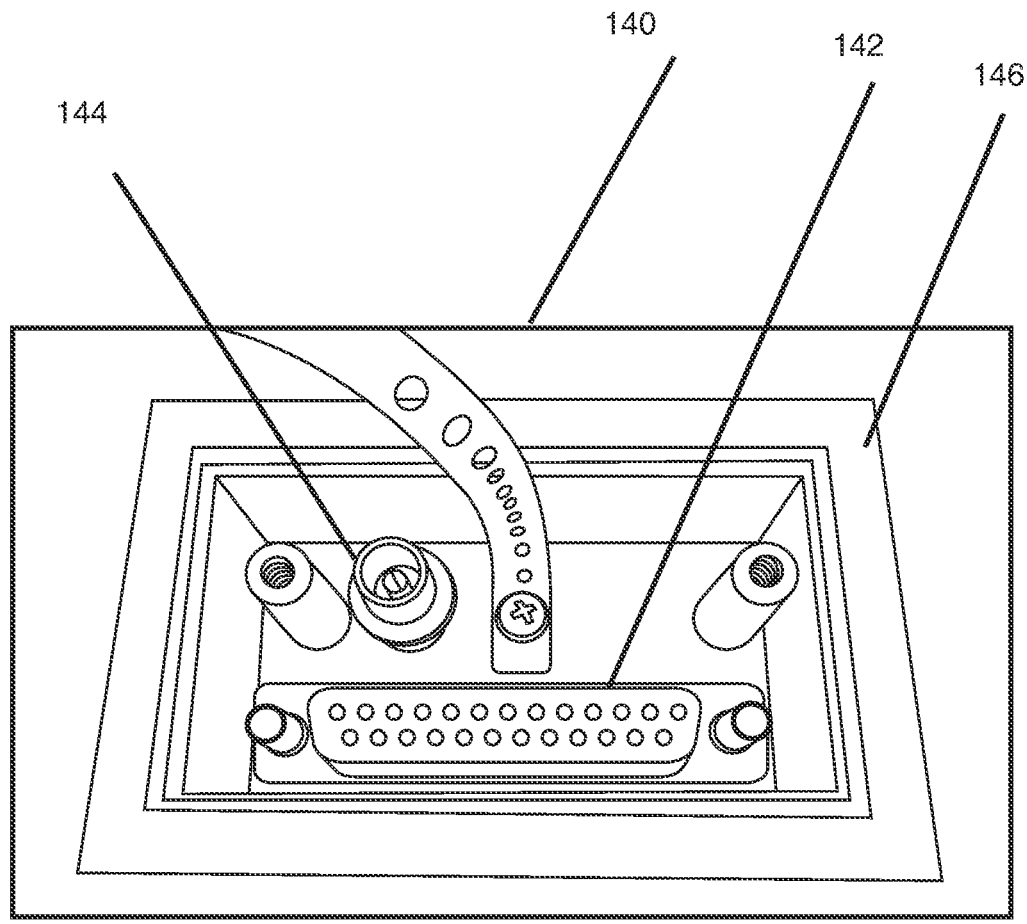
FIG. 16 illustrates an enlarged view of the communications port of FIG. 14 according to one or more embodiments disclosed herein.

FIG. 16 illustrates an enlarged view of the existing communications ports of the legacy gauge of FIGS. 14 and 15.

The adaptor is illustrated with a power module which may be provided for recharging batteries of the gauge, recharging batteries of the adaptor, providing operational power to the adaptor, or providing operational power to the gauge, or any combination thereof. The adaptor may include the antenna as illustrated, a GPS feature, and a communications port. The adaptor may include memory and a processor, and may be configured to store the measurements from the gauge until ready for transmission, such as, for example, in a situation where network service is unavailable.

One or more methods are provided herein. The one or more methods may include providing adaptor 40 as a "retro fit" to a legacy gauge 1. The gauge 1 is then placed into position for measurement. The mobile device then establishes communication with the adaptor The operator then directs the gauge 1 through the mobile device communicating with the adaptor 40 to take a measurement. The measurement data is then transmitted by the adaptor 40 to the mobile device through the network and a separate database that is communicated with also through the network.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, SSD or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs may be implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

As disclosed herein, adapter 40 is shown in communication with a material measurement gauge. However, adapter 40 may be employed with any device having a conventional communications port. This adapter with the appropriate firmware, may be tailored to a specific machine, and is also upgradable and expandable.

What is claimed:

1. A method comprising:
communicatively coupling a wireless device to a nuclear density gauge by mechanically attaching an adapter to the nuclear density gauge, the adapter including a processor configured to translate between a communication protocol of the wireless device and a legacy protocol of the nuclear density gauge, wherein mechanically attaching the adapter to the nuclear density gauge comprises plugging the adapter into an accessory port of the nuclear density gauge;
sending wirelessly, by the wireless device, a measurement request in the communication protocol of the wireless device;
receiving wirelessly, by the adapter, the measurement request in the communication protocol of the wireless device;
translating, by the processor of the adapter, the measurement request in the communication protocol of the wireless device to a measurement command in the legacy protocol of the nuclear density gauge, wherein the translating uses a translation software program of the adapter;
providing, by the adapter, the measurement command in the legacy protocol of the nuclear density gauge to the nuclear density gauge;
receiving, by the adapter, measurement data in the legacy protocol of the nuclear density gauge from the nuclear density gauge;
transferring, by the nuclear density gauge, the measurement data to the adapter;
converting, by the processor of the adapter, the measurement data in the legacy protocol of the nuclear density gauge to a measurement representative signal in the communication protocol of the wireless device;
sending wirelessly, by the adapter, the measurement representative signal in the communication protocol of the wireless device to the wireless device;
receiving wirelessly, by the wireless device, the measurement representative signal in the communication protocol of the wireless device; and
one of storing the measurement data for further operation on the wireless device and, if a calibration already exists, displaying, at the wireless device, a material property measurement value based on the measurement representative signal,
wherein the material property measurement value is calculated by: one of the nuclear density gauge and the wireless device; or the adapter and sent by the adapter to the wireless device,
wherein translating the measurement request from the communication protocol of the wireless device to the legacy protocol of the nuclear density gauge includes translating, by the translation software program of the adapter, between the legacy protocol of the nuclear density gauge and at least two modern communication protocols selected from: Bluetooth, universal serial bus (USB), WiFi, global positioning system (GPS), internet, local area network (LAN), cloud, and smart device communication formats.

2. The method of claim 1, comprising transferring, with the wireless device, the material property measurement value to a remote server.

3. The method of claim 2, wherein the material property measurement value is transferred after determining that a measurement step or a series of measurement steps is completed.

4. The method of claim 2, wherein the material property measurement value is transferred according to a predetermined polling schedule.

5. The method of claim 1, further comprising determining a location of the nuclear density gauge by determining a location with a location module on the wireless device.

6. The method of claim 1, further comprising determining a location of the nuclear density gauge by receiving location information from a location module communicatively coupled to the adapter on the nuclear density gauge.

7. The method of claim 1, further comprising determining a location of the nuclear density gauge by receiving location information from a location near the nuclear density gauge as determined by the wireless device.

8. The method of claim 1, wherein a location of the nuclear density gauge is determined at or about the time of receiving wirelessly, by the wireless device, the measurement representative signal in the communication protocol of the wireless device.

9. The method of claim 1, wherein the wireless device is one of a mobile and a non-mobile device.

10. The method of claim 1, wherein mechanically attaching the adapter to the nuclear density gauge comprises opening a portion of the nuclear density gauge and installing the adapter.

11. The method of claim 1, wherein at least a portion of the measurement data is uploaded to the wireless device and the wireless device: calculates at least one calibration constant based at least on the uploaded portion of the measurement data; and sends the at least one calibration constant to one of the nuclear gauge, and adapter.

12. The method of claim 1, wherein translating comprises transforming voltage levels and timing in the legacy protocol of the nuclear density gauge to the communication protocol of the wireless device.

13. The method of claim 1, wherein at least a portion of the measurement data is uploaded to the wireless device and the wireless device: calculates at least one calibration constant based at least on the uploaded portion of the measurement data; and sends the at least one calibration constant to one of the nuclear gauge, and adapter, wherein the wireless device comprises a wireless smart phone or wireless tablet.

14. A method comprising:
communicatively coupling an additional device to a nuclear density gauge by mechanically attaching an adapter to the nuclear density gauge, the adapter including a processor configured to translate, using a translation software program of the adapter, between a communication protocol of the additional device and a legacy protocol of the nuclear density gauge, wherein mechanically attaching the adapter to the nuclear density gauge comprises plugging the adapter into an accessory port of the nuclear density gauge;
transferring, by the nuclear density gauge, the measurement data to the adapter;
receiving, by the adapter, measurement data in the legacy protocol of the nuclear density gauge from the nuclear density gauge;
converting, by the processor of the adapter, the measurement data in the legacy protocol of the nuclear density gauge to a measurement representative signal in the communication protocol of the additional device;
sending, by the adapter, the measurement representative signal in the communication protocol of the additional device to the additional device; and
storing the measurement data for further operation on the additional device and, if a calibration already exists, displaying, at the additional device, a material property measurement value based on the measurement representative signal,
wherein the material property measurement value is calculated by: one of the nuclear density gauge and the additional device; or the adapter and sent by the adapter to the additional device,
wherein the translation software program of the adapter is further configured to translate, between the legacy protocol of the nuclear density gauge and at least two modern communication protocols selected from: Bluetooth, universal serial bus (USB), WiFi, global positioning system (GPS), internet, local area network (LAN), cloud, and smart device communication formats.

15. The method of claim 14, wherein the additional device comprises at least one of a remote server and the cloud.

16. The method of claim 14, wherein the additional device comprises a mobile device.

17. The method of claim 16, wherein the mobile device is configured to transmit a material property measurement value to a server.

18. The method of claim 14, wherein the additional device is a portable memory storage device.

19. The method of claim 14, further comprising determining a location of the nuclear density gauge.

20. The method of claim 14, further comprising receiving, at the adapter, a location of the nuclear density gauge from a location module on the nuclear density gauge.

21. The method of claim 14, wherein mechanically attaching the adapter to the nuclear density gauge comprises opening a portion of the nuclear density gauge and installing the adapter.

22. The method of claim 14, wherein the processor of the adapter is configured to transform voltage levels and timing in the legacy protocol of the nuclear density gauge to the communication protocol of the additional device.

23. A system comprising:
a gauge configured to generate measurement data indicative of one or more properties of a construction material;
an adapter communicatively coupled to the gauge by mechanical attachment to the gauge, the adapter including a processor configured to translate, using a translation software program of the adapter, between a legacy protocol of the gauge and at least two modern communication protocols selected from: Bluetooth, universal serial bus (USB), WiFi, global positioning system (GPS), internet, local area network (LAN), cloud, and smart device communication formats, wherein the adapter is mechanically attached to the gauge by plugging the adapter into an accessory port of the gauge, and wherein the adapter receives a transfer of measurement data from the gauge; and
a mobile device configured for:
wirelessly sending a measurement request in at least one of the at least two modern communication protocols;
receiving wirelessly from the adapter, by the mobile device and in at least one of the at least two modern communication protocols, a measurement representative signal converted by the adapter from measurement data in the legacy protocol of the gauge, wherein a material property measurement value is calculated by: one of the gauge and the mobile device; or the adapter and sent by the adapter to the mobile device.

24. The system of claim 23, wherein the mobile device is in communication with a network for transmitting a material property measurement value based on the measurement representative signal.

25. The system of claim 23, wherein the gauge includes a location module and the adapter communicates a location to the mobile device.

26. The system of claim 23, wherein the adapter includes a location module that reads a location that is communicated to the mobile device.

27. The system of claim 23, wherein the mobile device includes a location module that reads a location that is one of communicated to a network and stored internally along with a material property measurement value based on the measurement representative signal.

28. The system of claim 23, wherein the processor of the adapter is configured to transform voltage levels and timing in the legacy protocol of the gauge to the at least two modern communication protocols.

29. A kit comprising:
an adapter configured for communicative coupling to a gauge, the adapter including a processor configured to translate, using a translation software program of the adapter, between a legacy protocol of the gauge and at least two modern communication protocols selected from: Bluetooth, universal serial bus (USB), WiFi, global positioning system (GPS), internet, local area network (LAN), cloud, and smart device communication formats, wherein the adapter is configured to be mechanically attached to the gauge by plugging the adapter into an accessory port of the gauge and to receive a transfer of measurement data from the gauge; and a mobile device configured for:
wirelessly sending a measurement request in at least one of the at least two modern communication protocols;
receiving wirelessly from the adapter, by the mobile device and in the at least two modern communication protocols, a first measurement representative signal converted by the adapter from measurement data in the legacy protocol of the gauge; and
sending a second measurement representative signal, the second measurement representative signal based on the first measurement representative signal,
wherein a material property measurement value is calculated by: one of the gauge and the mobile device; or the adapter and sent by the adapter to the mobile device.

30. The kit of claim 29, wherein the adapter is fastened to an existing port location of the gauge, and is water tight.

31. The kit of claim 29, wherein sending the second measurement representative signal comprises wirelessly sending the second measurement representative signal across a network.

32. The kit of claim 29, wherein sending the second measurement representative signal comprises sending the second measurement to a memory location of the mobile device.

33. The kit of claim 29, wherein the processor of the adapter is configured to transform voltage levels and timing in the legacy protocol of the gauge to the at least two modern communication protocols.

34. A system comprising:
a material measurement gauge configured to generate measurement data indicative of at least one material property and including a gauge communications module; and an adapter configured for communicative coupling to the material measurement gauge by mechanical attachment to the gauge communications module, the adapter including a processor configured to translate, using a translation software program of the adapter, between a legacy protocol of the material measurement gauge and at least two modern communication protocols selected from: Bluetooth, universal serial bus (USB), WiFi, global positioning system (GPS), internet, local area network (LAN), cloud, and smart device communication formats and to communicate, in the at least two modern communication protocols to an additional device, a measurement representative signal converted by the adapter from measurement data in the legacy protocol of the material measurement gauge, wherein the adapter is configured to be attached to the material measurement gauge by plugging the adapter into an accessory port of the material measurement gauge, and to receive a transfer of measurement data from the material measurement gauge, wherein a material property measurement value is calculated by: one of the gauge and the mobile device; or the adapter and sent by the adapter to the mobile device.

35. The system of claim 34, wherein the additional device is a removable memory device.

36. The system of claim 34, wherein the additional device is a mobile device with which the adapter communicates wirelessly.

37. The system of claim 34, wherein the processor of the adapter is configured to transform voltage levels and timing in the legacy protocol of the gauge to the at least two modern communication protocols.

* * * * *